(12) United States Patent
Hammerstrom et al.

(10) Patent No.: US 7,037,468 B2
(45) Date of Patent: May 2, 2006

(54) DECONTAMINATION OF FLUIDS OR OBJECTS CONTAMINATED WITH CHEMICAL OR BIOLOGICAL AGENTS USING A DISTRIBUTED PLASMA REACTOR

(75) Inventors: Donald J. Hammerstrom, West Richland, WA (US); Joseph G. Birmingham, Richland, WA (US); James S. Millar, West Richland, WA (US)

(73) Assignee: MesoSystems Technology, Inc., Albuquerque, NM (US)

( * ) Notice: Subject to any disclaimer, the term of this patent is extended or adjusted under 35 U.S.C. 154(b) by 207 days.

(21) Appl. No.: 10/193,089

(22) Filed: Jul. 9, 2002

(65) Prior Publication Data

US 2002/0175068 A1    Nov. 28, 2002

Related U.S. Application Data

(62) Division of application No. 09/311,944, filed on May 14, 1999, now Pat. No. 6,455,014.

(51) Int. Cl.
    *B01J 19/08*    (2006.01)
(52) U.S. Cl. .................... 422/22; 204/164; 588/227
(58) Field of Classification Search ............. 422/22; 204/164; 588/227
    See application file for complete search history.

(56) References Cited

U.S. PATENT DOCUMENTS

| | | | |
|---|---|---|---|
| 3,205,162 A | 9/1965 | MacLean | 204/312 |
| 4,243,506 A | 1/1981 | Ikeda et al. | 204/298 |
| 4,954,320 A | 9/1990 | Birmingham et al. | 422/186.04 |
| 5,052,382 A | 10/1991 | Wainwright | 128/202.25 |
| 5,190,703 A | 3/1993 | Rose et al. | 422/186.05 |
| 5,194,291 A | 3/1993 | D'Aoust et al. | 148/276 |
| 5,215,636 A | 6/1993 | Danilychev et al. | 204/164 |

(Continued)

OTHER PUBLICATIONS

Vogtlin, George E. "Pulsed Plasma Processing of Effluent Pollutants and Toxic Chemicals." Mar. 12, 1999. Available: http://www-dsed.IInl.gov/documents/pulser_tech/gv-petta93_base.html.

*Primary Examiner*—Kishor Mayekar
(74) *Attorney, Agent, or Firm*—Ronald M. Anderson

(57) ABSTRACT

Apparatus and method for using a non-thermal plasma or corona discharge generated at multiple points and distributed to decontaminate surfaces and objects contaminated with chemical or biological agents. The corona discharge can be generated using very short high voltage pulses. The pulsed corona discharge can be directed at a contaminated surface through the unbraided strands at an end of a dielectric covered conductor. Another pulsed discharge embodiment incorporates a primary coil surrounding a chamber having a void filled with a plurality of secondary coils. A silent corona discharge can be generated using a variety of different configurations of a dielectric coated electrode and a bare electrode. The silent discharge is produced at all intersections between the dielectric covered electrode and the bare electrode. In one embodiment the apparatus comprises a blanket-like structure that is useful for decontaminating surfaces or decontaminating a fluid passing between spaced-apart bare electrodes.

6 Claims, 10 Drawing Sheets

U.S. PATENT DOCUMENTS

| | | | |
|---|---|---|---|
| 5,534,232 A * | 7/1996 | Denes et al. | 422/186.26 |
| 5,545,379 A | 8/1996 | Gray | 422/186.04 |
| 5,741,460 A | 4/1998 | Jacob et al. | 422/22 |
| 5,824,277 A * | 10/1998 | Campos et al. | 423/242.1 |
| 5,855,855 A | 1/1999 | Williamson et al. | 422/186.04 |
| 5,866,081 A | 2/1999 | Williamson et al. | 422/186.04 |
| 5,872,426 A | 2/1999 | Kunhardt et al. | 313/582 |
| 5,935,339 A * | 8/1999 | Henderson et al. | 134/1 |
| 6,200,539 B1 * | 3/2001 | Sherman et al. | 216/67 |
| 6,245,299 B1 | 6/2001 | Shiloh et al. | 422/121 |
| 6,406,759 B1 * | 6/2002 | Roth | 427/562 |

* cited by examiner

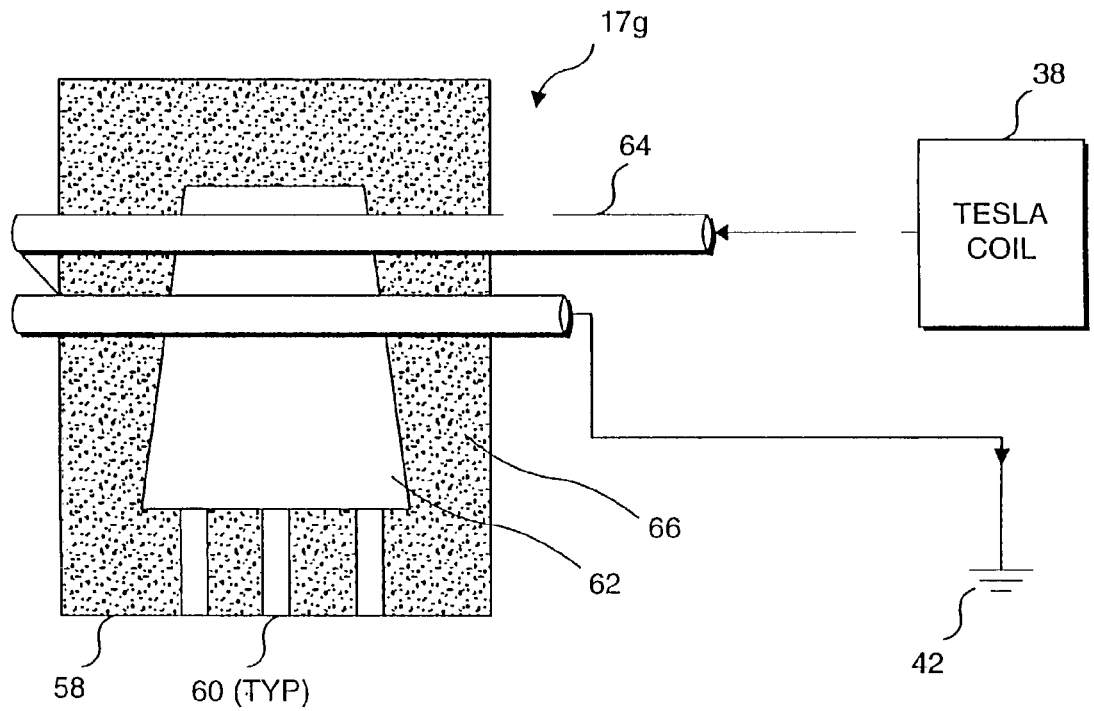
FIG. 13
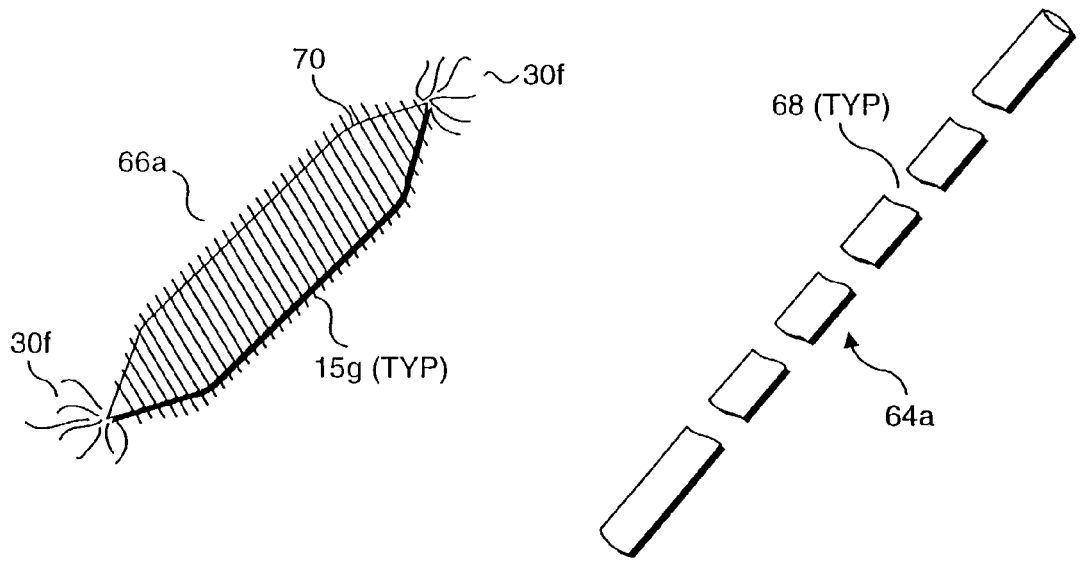
FIG. 14
FIG. 15

DECONTAMINATION OF FLUIDS OR OBJECTS CONTAMINATED WITH CHEMICAL OR BIOLOGICAL AGENTS USING A DISTRIBUTED PLASMA REACTOR

This application is a divisional application, based on prior application Ser. No. 09/311,944, now U.S. Pat. No. 6,455, 014 filed on May 14, 1999, the benefit of the filing date of which is hereby claimed under 35 U.S.C. § 120.

GOVERNMENT RIGHTS

This invention was made under contract with the United States Department of Defense, under Contract Numbers N68335-98-C-0211 and F49620-98-0079, and the United States government may have certain rights in the invention.

FIELD OF THE INVENTION

This invention relates to the decontamination of fluids, surfaces and objects, and more specifically to the use of an energy source for the decontamination of fluids, surfaces and objects contaminated with chemical or biological agents.

BACKGROUND OF THE INVENTION

The use of a non-thermal plasma to destroy pollutants is known. A non-thermal plasma is a plasma in which electrons, rather than a gas, are excited. Ozone generators commonly use a non-thermal plasma to produce ozone. Devices that produce non-thermal plasmas are often referred to as corona discharge generators. These devices generally operate by using very short duration, high voltage pulses (pulsed corona discharge) applied to an electrode. A corona discharge generator that employs a dielectric coating on the electrode is sometimes referred to as a barrier or silent corona discharge device. Tesla coils are often used as the high voltage source for a pulsed corona discharge; however, the pulsed corona discharge produced by a Tesla coil is often quite loud.

Recently, non-thermal plasmas have been used to remove pollutants from gas streams. U.S. Pat. No. 4,954,320, "Reactive Bed Plasma Air Purification," describes one such use of a non-thermal or corona discharge device used to detoxify a gas stream by passing the gas stream through a non-thermal plasma. The reactive bed plasma device described therein produces an active plasma, which yields energetic free electrons and highly reactive chemical species, especially oxygen atoms, to promote rapid oxidative decomposition of the contaminants in the air stream. This oxidation is similar to the process of incineration with the most notable difference being the dramatically reduced operating temperatures of the reactive bed plasma device. Electron impact is the driving force of plasma-induced decomposition, because it creates more free electrons, ions, reactive neutrals, and radicals. Another result of direct energy input at the quantum level is the emission of ultraviolet light from nitrogen molecules in the surrounding air. This ultraviolet radiation is capable of breaking some chemical bonds, ionizing many compounds, and disinfecting selected biological contaminants upon prolonged exposure.

While the prior art seems to suggest that a non-thermal plasma may be useful for treating a stream of gas, there is much less teaching of how to apply a non-thermal plasma to the decontamination of a surface or an object. Experimental chambers have been constructed to batch treat small objects with a non-thermal plasma. While such chambers can be useful in treating small, easily handled objects, it would be desirable to develop a system that enables a non-thermal plasma to destroy contaminants on the surfaces of large objects. It would further be desirable to develop a decontamination system that can distribute a non-thermal plasma to a wide variety of contaminated materials, including surfaces, objects, and fluids. The prior art does not teach or suggest how such a distributed non-thermal plasma generator can be achieved to provide for the independent or simultaneous decontamination of surfaces, object, or fluids.

While generally planar surfaces can be decontaminated using a non-thermal plasma generator that does not exhibit much dimensional flexibility, the decontamination of an irregularly-shaped object having non-planar surfaces would require a non-thermal plasma generator sufficiently large and flexible enough to drape over the object, so that the non-thermal plasma can "blanket" the object to be treated. The prior art does not teach or suggest how such a dimensionally flexible non-thermal plasma generator can be achieved.

An additional drawback of prior art non-thermal plasma generators is their relatively high power requirements. While such power levels as required for prior art devices may be readily supplied for compact non-thermal plasma generators, substantially larger non-thermal plasma generators will require correspondingly greater levels of power. Thus, a relatively large non-thermal plasma generator could not be easily powered by a portable power source, such as a battery. It is desirable that a non-thermal plasma generator based decontamination system scaled up to a relatively large size (able to decontaminate an object the size of a vehicle, for example) should still require power levels providable by portable power supplies. It would be further desirable that smaller non-thermal plasma generator based decontamination systems be powered by small batteries, such that non-thermal plasma generator based decontamination systems can be incorporated into small products such as personal air purifying respirators (APRs). The prior art also does not teach or suggest such systems.

While the prior art teaches using a non-thermal plasma to destroy the pollutants in a gas stream, there exists a wide range of chemical and biological agents that can contaminate surfaces, objects, or fluids, the destruction of which is not discussed in the prior art. Releases of chemicals from farms, factories and homes can contaminate soils. Fungi and spores can contaminate seeds and foodstuffs, and even the soil used to grow crops. Disease causing microorganisms are frequently present on surfaces, objects, and within the air. Allergens and toxins are frequently present in the outside ambient air, as well as the air within buildings (i.e., the "sick building syndrome").

Additionally, potential terrorist use of chemical and biological agents represents an ever-growing threat to populations and property. The release of the chemical warfare agent Sarin in the Tokyo subway system by the Aum Shinrikyo cult has drawn widespread attention to the potential use of chemical and biological agents in attacks by terrorist or dissident groups. Also of concern is the fact that use of chemical and biological warfare agents by foreign powers during military actions seems much more likely in view of events in the Middle East during the last decade. Military vehicles and other objects exposed to chemical and biological contamination represent a hazard if their surfaces are contacted by unprotected personnel. Decontamination of an area or object after the actual or suspected release of such agents thus poses significant challenges and risks.

It therefore would be desirable to develop a decontamination system that is effective against a wide range of biological and chemical agents, while minimizing incidental damage to the surface or object being decontaminated. It would further be desirable for such a decontamination system to have a low power requirement so that batteries or other readily portable power sources could be employed to energize the system. A desirable system of this type should operate at ambient pressure and temperature and should not consume large quantities of reagents nor produce large quantities of waste byproducts. A desirable decontamination system should be able to readily destroy contaminants disposed within cracks or crevices of a surface or object. Finally, such a system should be well adapted to decontaminating almost any fluid stream, such as breathing or medical air; as well as almost any surface, such as floors, desks, or walls, and more complex objects, such as irregularly-shaped tools, vehicles, and other equipment.

SUMMARY OF THE INVENTION

In accord with the present invention, apparatus are defined for detoxifying chemical or biological agents. These agents may be on a surface or entrained in a fluid. The distributed plasma reactor apparatus includes a non-thermal plasma generator, which when activated by a sufficiently high voltage, produces a plasma discharge. The plasma discharge is adapted to be positioned in proximity to the chemical or biological agents so that reactants produced by the plasma discharge detoxify the chemical or biological agents. A power source capable of energizing the non-thermal plasma generator at a high voltage is electrically coupled to the non-thermal plasma generator to activate it.

In one preferred embodiment, the distributed plasma reactor comprises a large surface of distributed electrodes, or "plasma blanket," which is adapted to be disposed adjacent to a surface to be decontaminated, such that the plasma discharge is produced near the surface. Preferably, the plasma blanket is sufficiently flexible to drape over an irregularly-shaped object having non-planar surfaces that are to be decontaminated.

For portable applications, the power source comprises a battery and a high voltage inverter that converts a direct current produced by the battery to the high voltage used to activate the plasma generator.

In several embodiments, the distributed plasma reactor comprises a silent discharge type non-thermal plasma generator, while in other embodiments, the distributed plasma reactor comprises a pulse discharge type non-thermal plasma generator.

In the silent discharge type, the non-thermal plasma generator includes one or more dielectric covered electrodes and one or more bare electrode that are connected to the power source so that the high voltage is applied between the dielectric covered electrodes and the bare electrodes. In one embodiment, the bare electrode is formed in an accordion-folded pleated configuration and the dielectric covered electrodes pass through adjacent pleats of the bare electrode.

To decontaminate a larger area, the distributed plasma reactor includes a plurality of dielectric covered electrodes and may include a plurality of bare electrodes. In one preferred form, the bare electrode comprises a conductive mesh that is relatively flexible.

One embodiment of a plasma blanket includes a sheet of non-conductive material that is substantially parallel to the plurality of dielectric covered electrodes. This sheet serves to direct the plasma discharge onto the surface to be decontaminated.

In one preferred embodiment, the bare electrode is helically wrapped around the dielectric covered electrode. A plurality of bare and dielectric covered electrodes of this type can be attached to and supported by a flexible substrate.

The bare electrode can be formed as a sheet, which may comprise a metal foil, or a conductive mesh. The dielectric covered electrode preferably extends through the bare electrode. Two or more bare electrodes configured as sheets can be spaced apart from each other in parallel, to define a treatment volume through which a contaminated fluid is conveyed.

A plasma discharge is produced at each intersection where a bare electrode and a dielectric covered electrode overlap, intersect, or where the bare electrode is helically coiled about the dielectric covered electrode.

In another embodiment of the distributed plasma reactor, a dielectric covered electrode has a first end electrically coupled to the power source, and a non-thermal corona discharge is generated at a second opposite end of the dielectric covered electrode. Preferably, the dielectric covered electrode further comprises a multi-stranded conductor, and at the second end of the dielectric covered electrode, the conductor is separated into individual strands, such that a non-thermal corona discharge is generated by each individual strand. This embodiment is excited by a high frequency pulsed source.

In still another embodiment, the distributed plasma reactor comprises a non-conductive substrate supporting a plurality of spaced-apart point electrodes and a plurality of spaced-apart dielectric spacers. The plurality of electrodes and the plurality of dielectric spacers are connected to a surface of the non-conductive substrate and extend away from the surface. The dielectric spacers extend substantially farther from the surface than the point electrodes to maintain a space between the point electrodes and the surface to be decontaminated, preventing the point electrodes from shorting to ground on that surface.

Another aspect of the present invention is directed to a method for decontaminating a substance by destroying a toxic material that has contaminated the substance. The method includes the step providing a power source that produces a voltage sufficiently great to generate a plasma discharge. A distributed plasma reactor is positioned proximate to the substance that is to be decontaminated. The distributed plasma reactor is then activated with the power source, producing a non-thermal plasma discharge that destroys the toxic material, thereby decontaminating the substance. Other functional steps of the method are generally consistent with the description of the apparatus set forth above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 schematically illustrates a portion of a barrier or silent corona discharge generator;

Figure 6A:
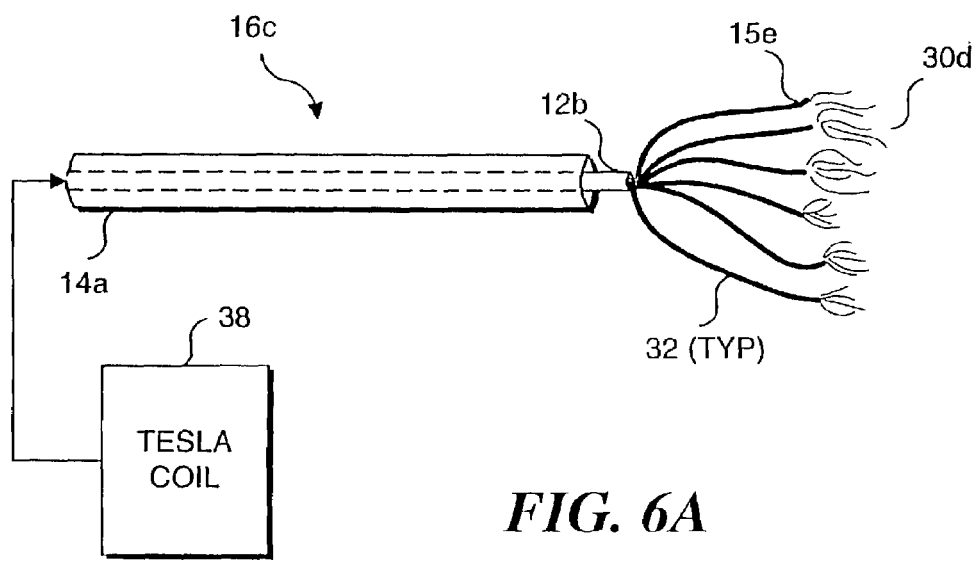
Figure 6B:
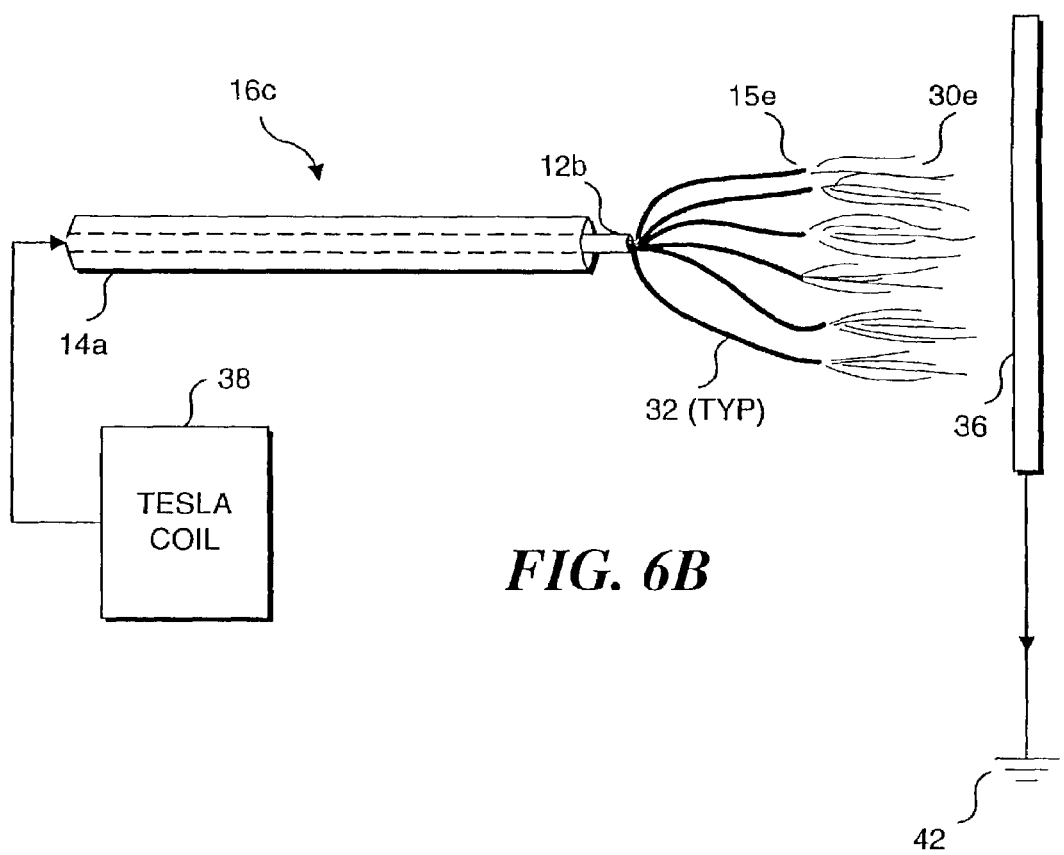
Figure 7:
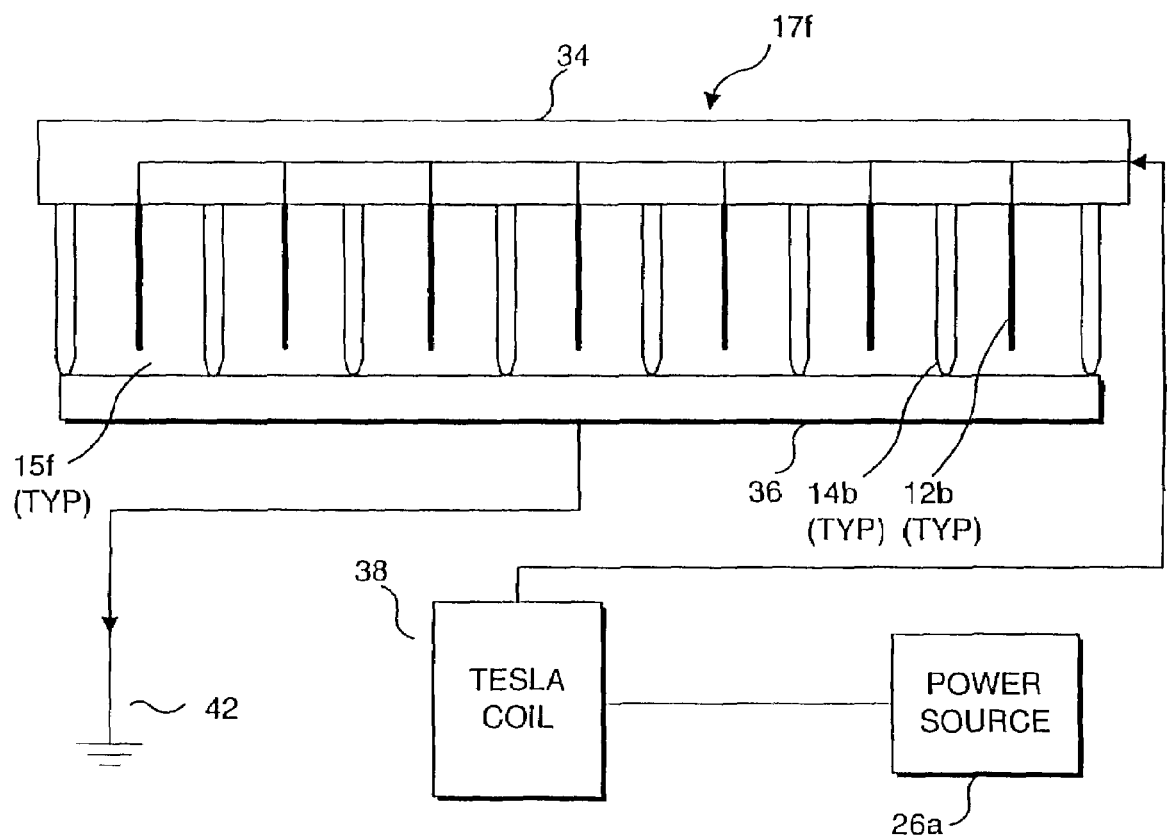
Figure 8A:
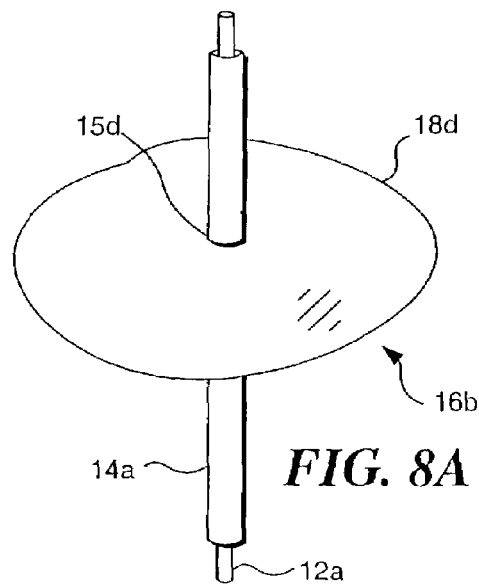
Figure 8B:
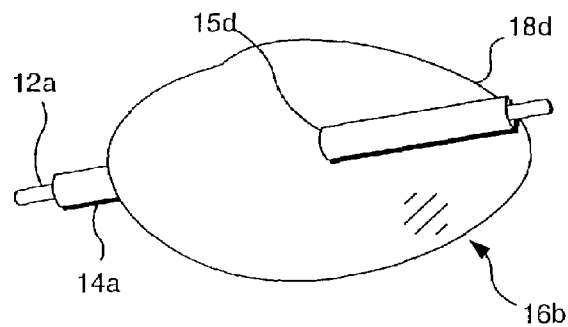
Figure 9:
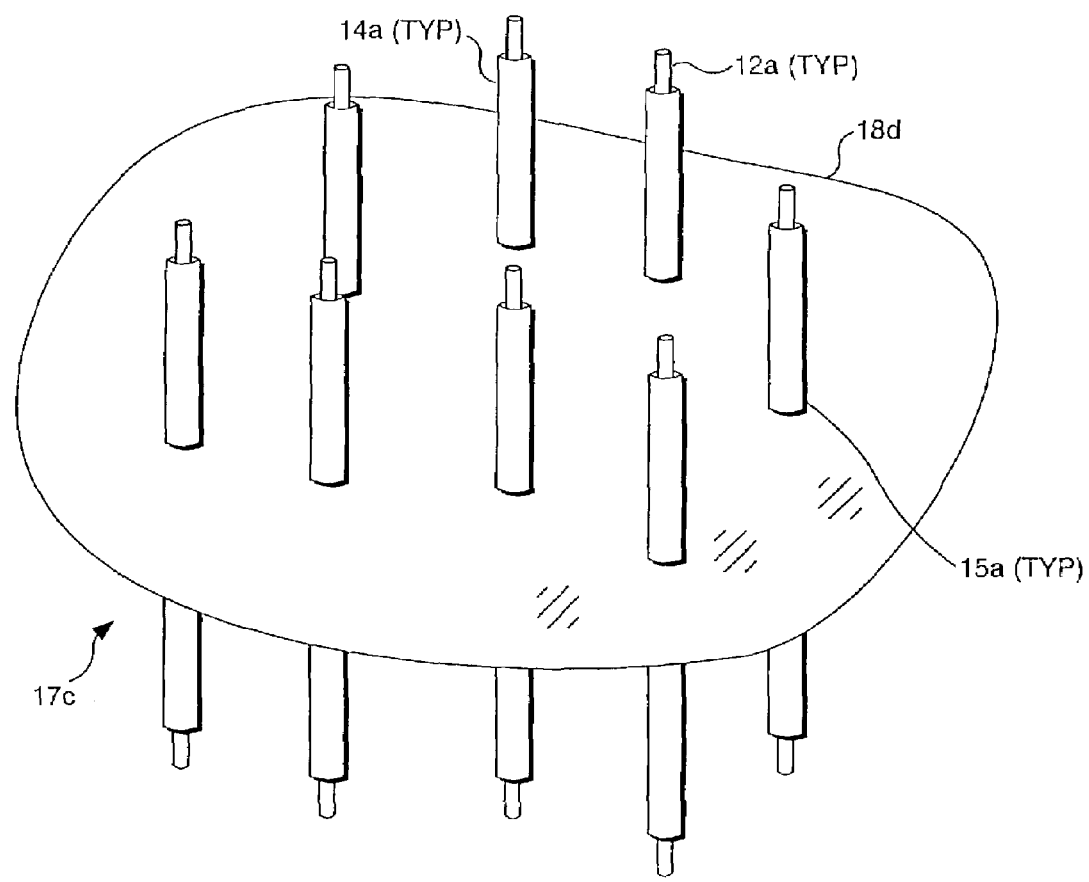
Figure 10:
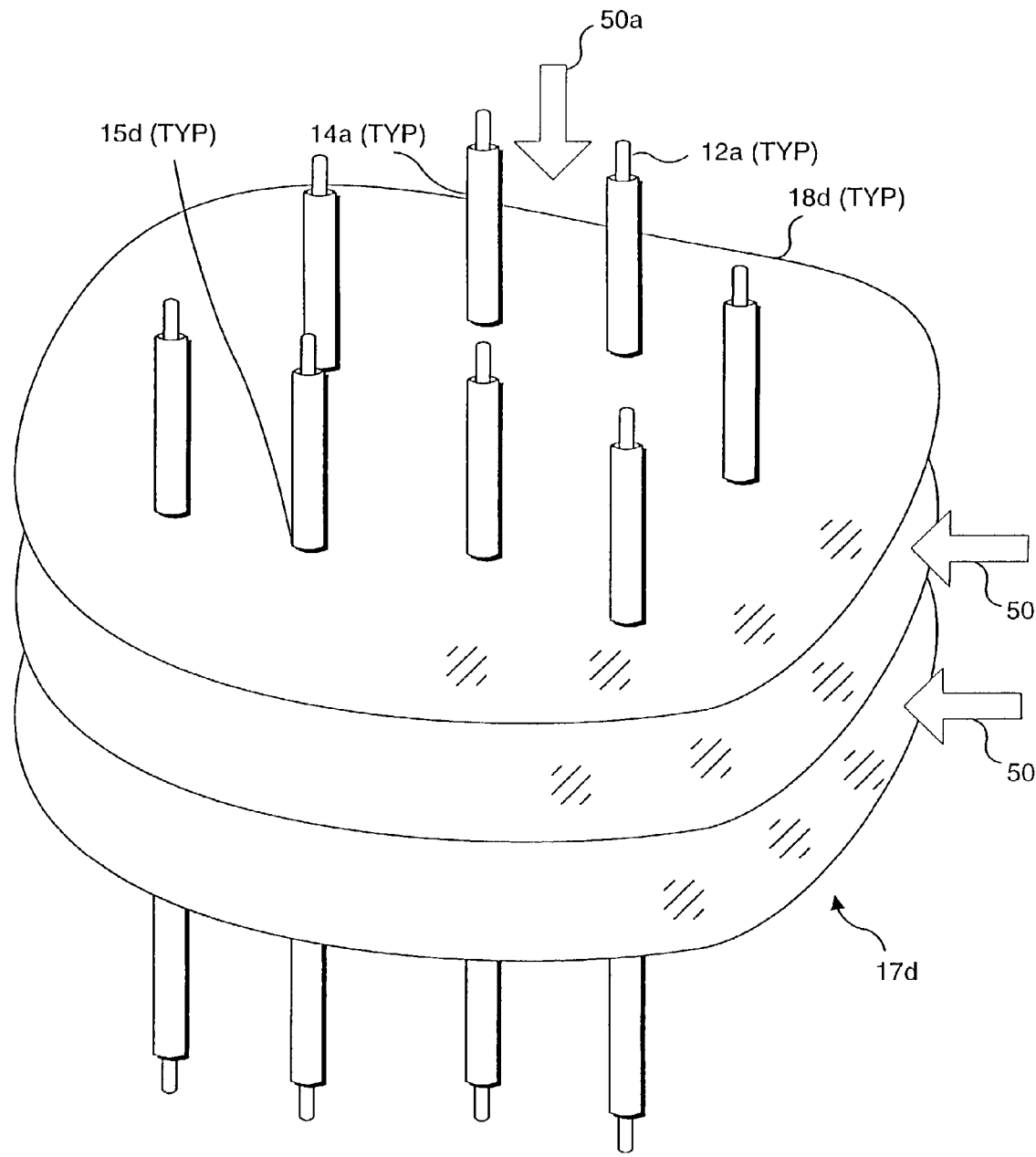
Figure 11:
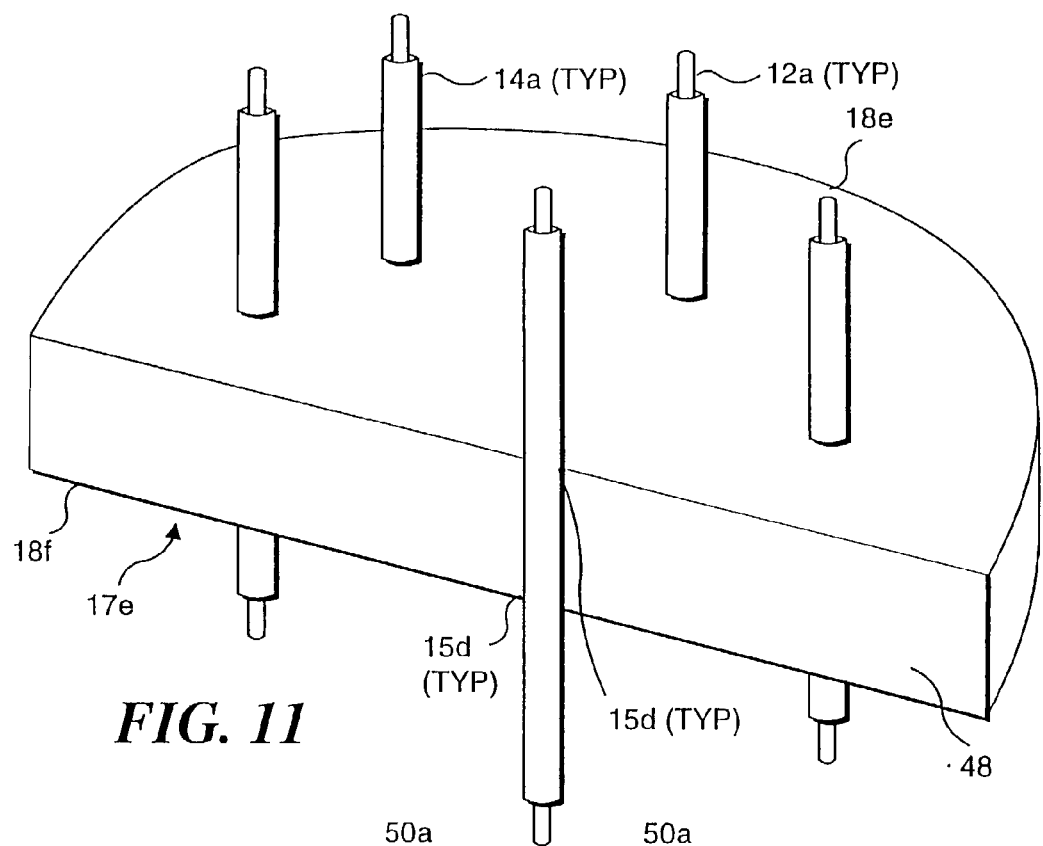
Figure 12:
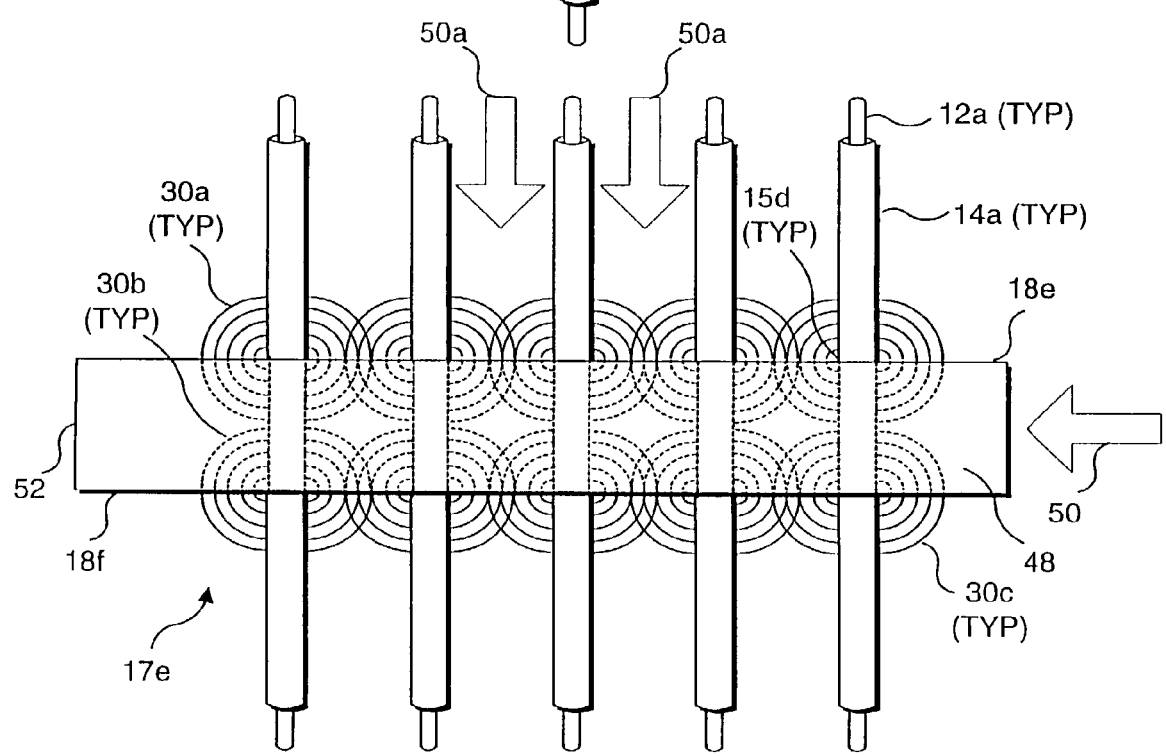
Figure 16:
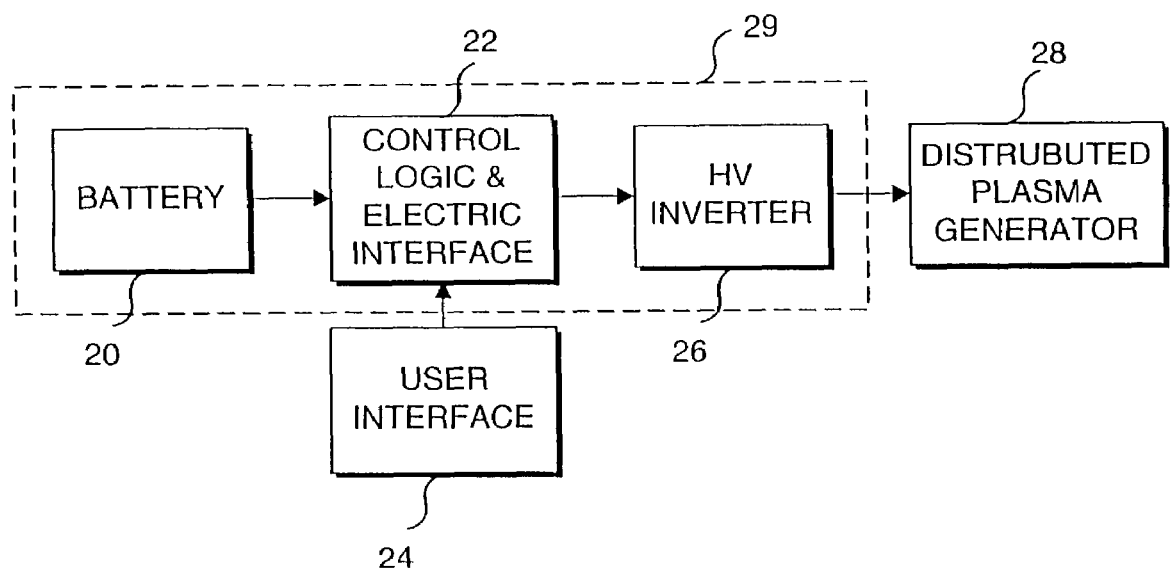

FIGS. 6A and 6B schematically illustrate a pulsed corona discharge generator having a dielectric covered braided electrode terminating in a plurality of individual strands, energized by a Tesla coil;

FIG. 7 is a schematic view of a plasma blanket comprising distributed plasma reactors of the pulsed discharge type that includes a plurality of bare pin electrodes on a supporting substrate, and dielectric spacers to maintain the bare electrodes spaced apart from a grounded surface;

FIGS. 8A and 8B are isometric views illustrating a silent corona discharge generator, showing a single dielectric covered electrode passing vertically and at an acute angle through a bare electrode sheet, respectively;

FIG. 9 is an isometric view schematically illustrating a portion of a distributed plasma reactor comprising a plurality of silent corona discharge generators like those shown in FIGS. 8A and 8B;

FIG. 10 is an isometric view schematically illustrating a portion of a distributed plasma reactor in which a plurality of dielectric covered electrodes like those shown in FIGS. 8A and 8B pass through a plurality of spaced-apart bare electrode sheets;

FIG. 11 is a cross-sectional isometric view of an embodiment of a distributed plasma reactor in which the bare electrodes define a volume through which a contaminated fluid flows;

FIG. 12 is an elevational view of the embodiment of FIG. 11;

FIG. 13 is a schematic view of a distributed plasma reactor of the pulsed discharge type that includes a primary coil surrounding an internal treatment volume that is completely packed with a plurality of small secondary coils;

FIG. 14 is an isometric schematic view of one of the secondary coils used to fill the void spaces of the treatment volume in the distributed plasma reactor of FIG. 13;

FIG. 15 is an isometric schematic view of a primary coil that includes a plurality of spark gaps for use with the distributed plasma reactor of FIG. 13; and FIG. 16 is a block diagram identifying the functional component of a portable distributed plasma reactor decontamination system in accord with the present invention.

DESCRIPTION OF THE PREFERRED EMBODIMENT

In accord with the present invention, a non-thermal plasma or corona discharge is employed to decontaminate fluid streams, objects and surfaces that have been contaminated with chemical or biological agents. Such contaminants are expected to include, but are not limited to, chemical agents, biological agents, chemical and biological warfare agents, disease causing microorganisms, allergens, molds and fungi. Preferably such a discharge is generated at multiple locations throughout a given treatment volume to ensure the plasma is thoroughly distributed throughout the treatment volume, such that overlapping zones of a non-thermal plasma produced thereby can be used to decontaminate a selected surface, object, or volume. An important feature of the present invention is that non-thermal plasma based decontamination systems can be fabricated that have very low power requirements, and which require low excitation voltages. A further novel feature of the present invention is that desired decontamination systems can be fabricated which exhibit a high degree of dimensional flexibility. The term "distributed plasma reactor" as used as used herein and in the claims that follow means an apparatus capable of generating a non-thermal plasma that can be distributed as multiple overlapping zones over a desired treatment area. Such a distributed plasma reactor can be configured such that the apparatus requires minimal power to provide the decontamination effect even for a relatively large treatment area. The non-thermal plasma is produced by either a silent/barrier discharge generator or a pulsed discharge generator. A novel feature of the invention is that the bare electrode in the silent/barrier discharge generators can be in point contact with the dielectric covered electrode.

One purpose of the present invention is to provide apparatus that can generate a relatively large volume of plasma for use in decontaminating a correspondingly large volume, while minimizing the power and voltage requirements. Large volume plasma chambers have been built, but these prior art chambers typically require large excitation voltages because of the need to fill the large chamber with plasma. In contrast, the present invention reduces the voltage required by minimizing the distances between the electrodes, and by employing multiple electrodes to distribute the plasma throughout the volume. The multiple electrodes penetrate the treatment volume, so that multiple small volumes of plasma are generated using a much lower applied voltage than required in the prior art chambers. Sufficient electrodes penetrate the treatment volume such that the small plasma volumes generated completely fill the chamber. In embodiments utilizing a dielectric covered electrode and bare electrode, the bare electrode can be in point contact with the dielectric. This point contact reduces the voltage required to bridge the gap between the pair of electrodes.

In another embodiment, power consumption is reduced by minimizing the treatment volume required to treat a fixed contaminated volume. In this embodiment, instead of providing a large chamber that defines the extents of a fixed contaminated volume, a flexible apparatus is provided to "blanket" or envelop the contaminated volume. In this manner, the volume in which the plasma is generated and maintained is reduced to be just slightly larger than the contaminated volume. In a plasma chamber of a fixed size, unless the contaminated volume is essentially the same size as the plasma chamber, power is unnecessarily expended to create and fill the large chamber with a greater volume of plasma than is actually required to treat the contaminated object (or volume). By providing an apparatus that conforms to the volume of the thing that is to be treated, power consumption is substantially reduced.

Many surfaces that may become contaminated with chemical or biologic agents are likely to be generally planar. In a first preferred embodiment of the invention, a distributed plasma reactor comprises a blanket-like structure that can be placed over a surface to be decontaminated; the blanket-like structure produces a non-thermal plasma or corona discharge. As described above, such an embodiment would effectively minimize the treatment volume, and thus the power required to maintain a plasma. Since there is a need to decontaminate objects such as vehicles and weapons that have non-planar surfaces and irregular shapes, it will be apparent that the decontamination apparatus is preferably capable of accommodating non-planar surfaces. Accordingly, by making the blanket-like structure sufficiently flexible, the distributed plasma reactor can be draped over an object to be decontaminated, or the object may be wrapped in the distributed plasma generator. FIGS. 3–5 and 7 are directed to embodiments that use distributed plasma reactors comprising a blanket-like structure for decontaminating surfaces. For each of these embodiments, the non-thermal plasma is preferably generated by a multiplicity of distributed electrodes of the type shown in FIGS. 2, 8A, or 8B. The use of a plurality of such electrodes allows lower excitation voltages to be used, thus providing apparatus that incorporate the features of low excitation voltages and relatively low power consumption. These embodiments are collectively referred to as "plasma blankets."

The term "plasma blanket" as used herein means a distributed plasma reactor that is particularly well suited for use in decontaminating a surface or object. Preferably, unless an object is limited to a planar surface, a plasma blanket used for decontaminating the object should exhibit a high degree of dimensional flexibility so that the plasma blanket may drape over or be wrapped around the object. While plasma blankets are particularly well suited to decontaminate surfaces or objects, it should be noted that any fluid that is passed through or otherwise exposed to the non-thermal plasma generated by a plasma blanket will be similarly decontaminated. Thus, it should be understood that any embodiment of a plasma blanket described herein could also be used to decontaminate a fluid. It is envisioned that appropriately configured distributed plasma discharge reactors can be used for independently or simultaneously decontaminating surfaces, objects, and fluids.

Another preferred embodiment of the present invention uses distributed plasma reactors specifically for the treatment of fluids. As described above, in the embodiment of the present invention in which a plurality of electrodes penetrate the treatment volume, a relatively low excitation voltage can be used. FIGS. 9–12 are directed to embodiments that use distributed plasma reactors for treating fluids such as air. Such embodiments are particularly applicable for use in decontaminating air flowing through heating, ventilation, and air conditioning (HVAC) systems for building or vehicles. Smaller devices can be easily adapted for personal use, such as in air purifying respirators (APRs), because of the particularly modest power requirements of the distributed plasma generator. For these embodiments, the non-thermal plasma is preferably generated by a silent discharge generator.

An additional preferred embodiment of the present invention similarly distributes plasma throughout a treatment volume by generating the plasma at a plurality of locations. This embodiment comprises a treatment chamber encircled by a primary coil. The internal volume of the treatment chamber is filled with a plurality of small secondary coils. A sufficient quantity of the secondary coils can be supplied to fill any volume of the treatment chamber that is not occupied by the volume of the object to be treated. If the contaminated volume comprises a fluid rather than an object, the entire treatment volume can be filled with the secondary coils, and the fluid to be decontaminated may then be passed though the treatment volume. FIGS. 13–15 are directed to this embodiment.

Figure 1:
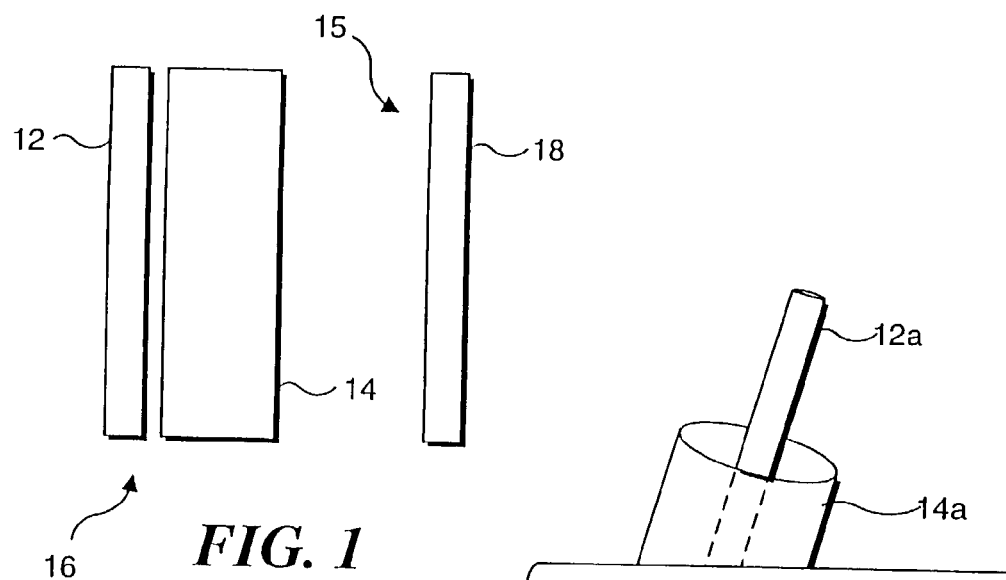

FIG. 1 shows the elements required at a minimum for constructing a silent or barrier corona discharge generator 16. Such a silent corona discharge generator can be beneficially incorporated into a distributed plasma reactor used for decontaminating fluids, surfaces, or objects. The generator includes a dielectric material 14, which shields an electrode 12. A gap 15 separates dielectric material 14 from a bare electrode 18. It is within gap 15 that the corona discharge occurs when a high voltage pulse produced by an appropriate source (not shown) is applied between electrode 12 and bare electrode 18. Any contaminated surface on which biological or chemical agents are disposed in proximity to the corona discharge is decontaminated by it, as described above in the Background of the Invention. While not shown, it should be noted that a silent or barrier corona discharge generator may be constructed using a dielectric covered electrode in place of bare electrode 18.

Empirical testing has determined that sustainable levels of non-thermal plasma can be generated by a distributed plasma reactor having an area of only a few square centimeters comprising an electrode fabricated of common $\frac{1}{32}$ inch diameter electrical wire, when energized by a battery power source (at about 1 watt/cm$^2$). A high efficiency inverter and transformer were used to provide a voltage of about 4,000 volts peak-to-peak to energize the distributed plasma reactor in this test. The combination of an electrode having a small radius of curvature with the compact and efficient inverter and transformer power sources currently available enable a wide range of distributed plasma reactors to be fabricated that can be energized with portable power supplies, so that small distributed plasma reactors, suitable for use a personal APR may be powered by very compact batteries. Larger distributed plasma reactors, such as one comprising a blanket-like structure that can be draped over a military vehicle like a tank, may be energized with larger, yet still portable power supplies.

It is important to note that a distributed plasma reactor comprising electrodes that have a very small radius of curvature tend to be inherently flexible, due to the small diameter of the electrodes. Thus, distributed plasma reactors that exhibit a large degree of dimensional flexibility can readily be fabricated in accord with the present invention. Such flexibility is quite useful when the surface or object to decontaminated is non-planar. It should also be noted that the material from which dielectric 14 shielded electrode 12 or bare electrode 18 are fabricated of is not critical, as long as it is a reasonable good electrical conductor. Electrodes can be wires, metal sheets, metal foils, or metal traces deposited on a substrate. Of course, if it is desirable that a distributed plasma reactor exhibit significant dimensional flexibility, then both of the electrodes, as well as dielectric 14, and any additional elements comprising the distributed plasma reactor must be dimensionally flexible. While not shown, it is important to note that bare electrode 18 can touch dielectric 14 without in anyway impairing the production of a non-thermal plasma. A non-thermal plasma will be generated at any point of contact between bare electrode 18 and dielectric 14.

Figure 2:
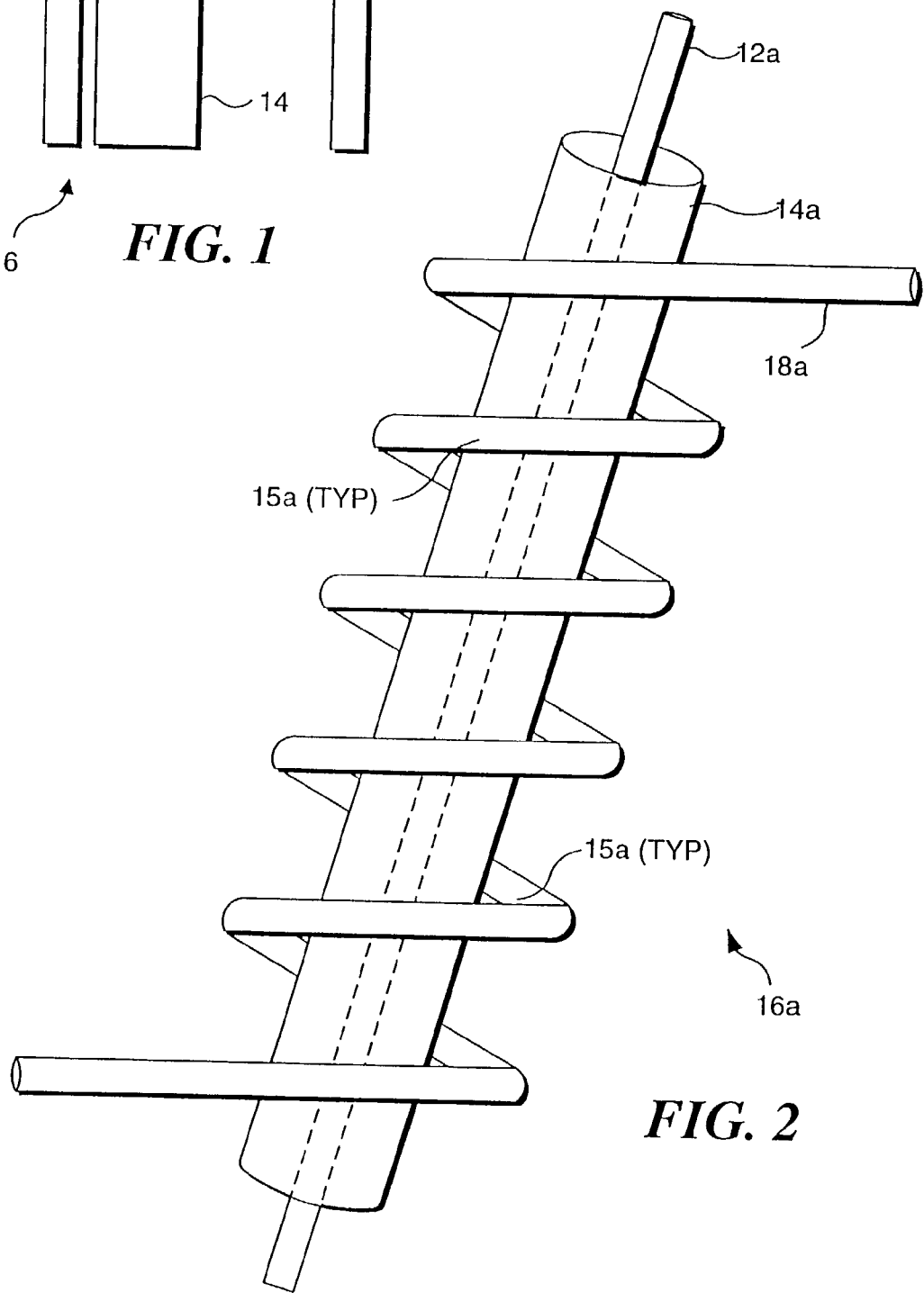
FIG. 2 is an isometric schematic view of an "inline" distributed plasma reactor of the silent discharge type having a bare electrode in a helical configuration, wrapping around a dielectric covered electrode.

FIG. 2 illustrates a first preferred embodiment of a distributed plasma reactor 16a, in which the plasma is distributed along a helical contact in accord with the present invention. Generator 16a includes an electrode 12a, which is surrounded by a dielectric material 14a. In a simple form of this embodiment, electrode 12a and dielectric material 14a can comprise a simple insulated wire of small diameter, such as the wire commonly used for electrical interconnections in electronic circuit assemblies. Preferably, however, electrode 12a is a bare wire electrode, and dielectric material 14a is a glass or quartz tube, but other dielectric materials can be used, including plastics and other materials that are relatively flexible and elastomeric, and the dielectric material can be in the form of fibers, beads, foam, or almost any other configuration that provides a dielectric barrier around electrode 12a.

Figure 5:
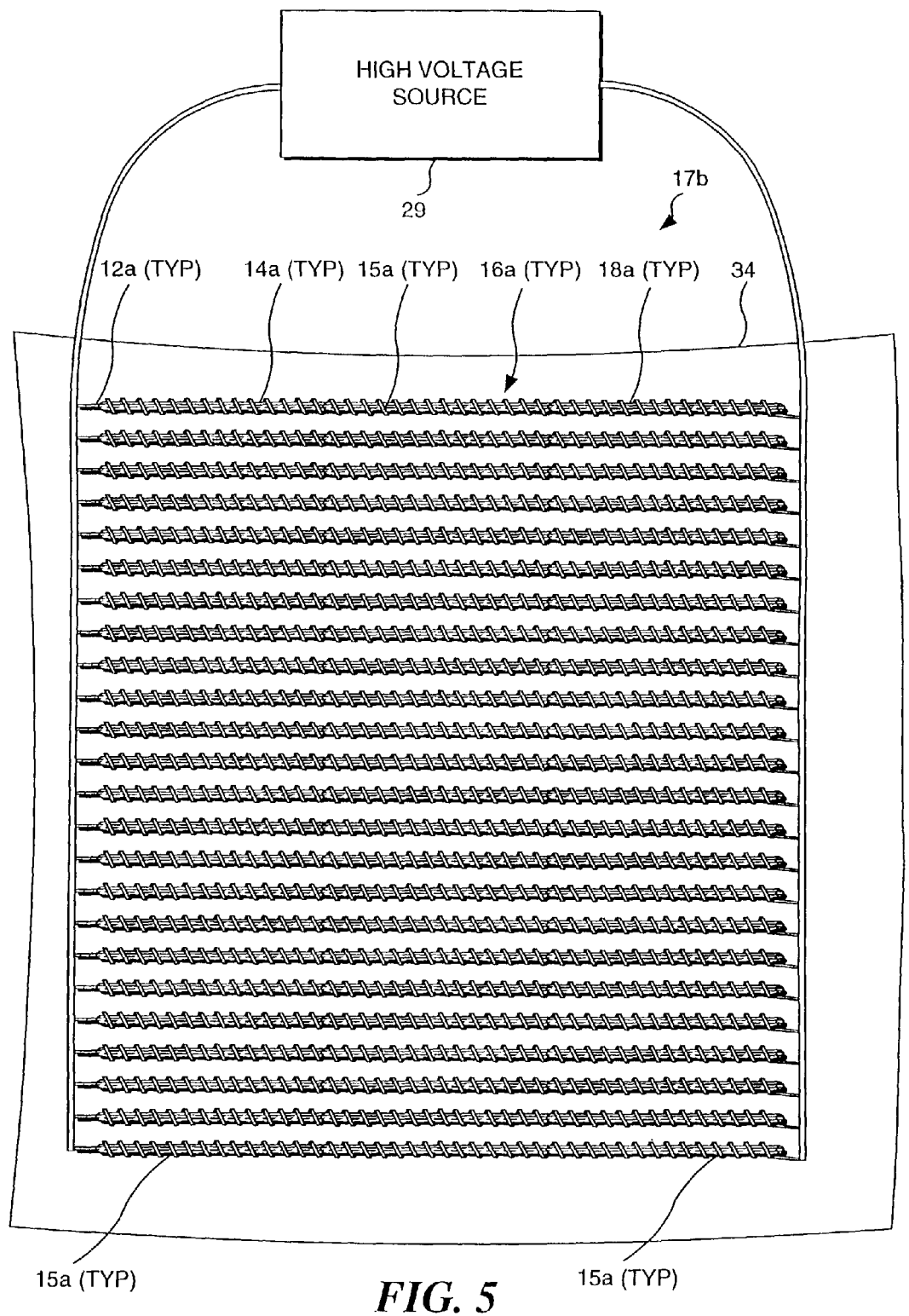
FIG. 5 is a schematic plan view of another embodiment of a plasma blanket that incorporates a plurality of flexible inline distributed plasma reactors of the silent discharge type, such as shown in FIG. 2, mounted on a flexible substrate.

In distributed plasma reactor 16a, a bare electrode 18a is helically coiled or plated around dielectric material 14a and may comprise a fine filament wire, a metallic tape, a metallic foil, or a metallic trace deposited directly onto dielectric 14a by lithography or vapor deposition methods. The corona discharge phenomenon generally occurs in a vicinity 15a where bare electrode 18a touches or crosses adjacent to dielectric material 14a, when a high voltage (e.g., 4,000 volts peak-to-peak) is applied between electrode 12a and bare electrode 18a. It is important to understand that a corona discharge will occur around bare electrode 18a anywhere it contacts or is adjacent to dielectric material 14a. Thus, the helical coil defined by bare electrode 18a around dielectric material 14a will generate a corona discharge when electrode 12a and bare electrode 18a are energized at different voltage potentials, and the effect of the corona discharge will extend radially beyond the limits of the bare electrode, so that any contaminated fluid or surface (not shown) in the vicinity of both the bare electrode and dielectric material 14a will be decontaminated by the resulting corona discharge and the ionized gas environment that it produces. While the area that can be decontaminated by a single distributed plasma reactor 16a is finite, multiple distributed plasma reactors 16a mounted on a flexible substrate to form a flexible plasma blanket, as is shown in FIG. 5, enable the decontamination of substantially larger areas or volumes. Details of FIG. 5 are discussed below.

Figure 3:
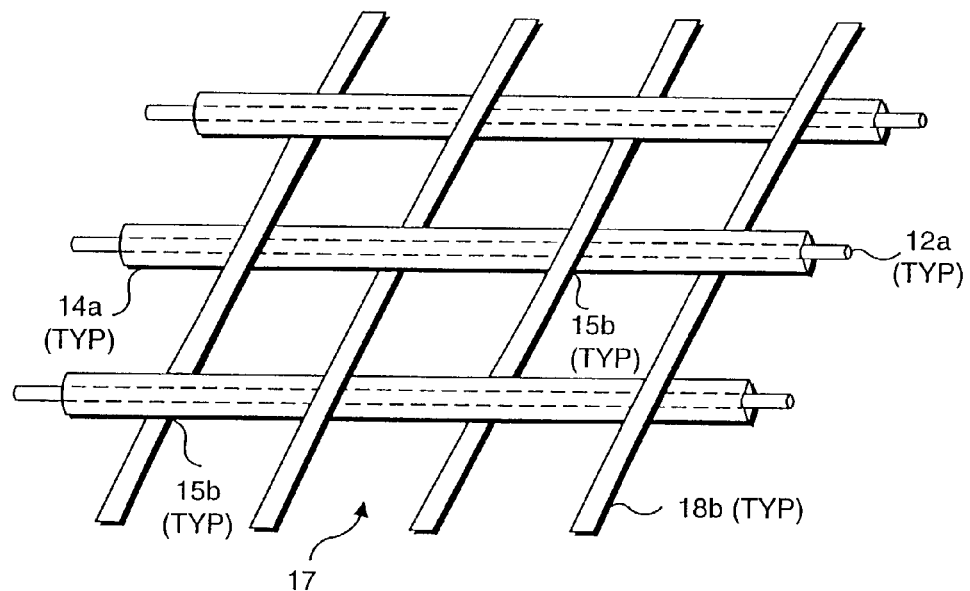
FIG. 3 is an isometric schematic view of a portion of a plasma blanket comprising a plurality of distributed plasma reactors of the silent discharge type in a woven configuration.

FIG. 3 illustrates a plasma blanket 17 having a woven configuration in which a plurality of electrodes 12a covered with dielectric material 14a, and a plurality of bare electrodes 18b, are woven substantially perpendicular to each other, producing a flexible plasma blanket of any desired dimensions. Again, the corona discharge phenomenon will occur at each intersection 15b of the dielectric material 14a covered electrodes 12a and bare electrodes 18b.

In a preferred embodiment, dielectric material 14a covered electrodes 12a and bare electrodes 18b are woven into a sheet or blanket sufficiently large in area to cover a surface or an object that is to be decontaminated. Such a blanket can then be placed onto a surface that is contaminated with any one or more of a chemical agent, a biological agent, a disease causing microorganism, an allergen, a spore, and/or a fungi. When the blanket is energized, the corona discharge will effectively destroy the contaminant. Preferably, dielectric material 14a covered electrodes 12a and bare electrodes 18a are flexible, so that the resulting plasma blanket will be sufficiently flexible to drape over an object, or to be wrapped around an object. Such a flexible blanket can then be used to decontaminate irregularly-shaped objects as well as flat surfaces.

Plasma blanket 17 can be woven only of bare electrodes 18b and dielectric material 14a covered electrodes 12a as shown, or the blanket can also include an additional non-conducting flexible material, such as fiberglass, natural or synthetic cloth threads, and other fibrous material. This flexible material (not shown) can be woven into a blanket, or used as a flexible substrate upon which dielectric material 14a covered electrodes 12a and bare electrodes 18b are mounted (for example, by stitching the dielectric material covered electrodes and bare electrodes onto the surface of the underlying substrate). Such a configuration should provide protection to the electrodes when the blanket is in use or storage. Furthermore, if the electrodes are mounted on a flexible substrate, the substrate will act to direct and contain the reactive species generated by the non-thermal plasma onto the contaminated surface. If the plasma blanket solely comprises the woven electrodes as shown in FIG. 3, the corona discharge plasma will be generated both above and below the plasma blanket, and the plasma produced on the side of the plasma blanket opposite that adjacent to the contaminated surface will have less effect in decontaminating the surface. In contrast, if the electrodes are supported by a blanket substrate, the plasma generated below the blanket substrate should be more directed at the contaminated surface and more efficiently decontaminate the surface. Another alternative would incorporate strips of the flexible cloth or fiber thread material into the spaces between adjacent dielectric material covered electrodes 12a and between adjacent bare electrodes 18b. While such a filler material is not be required, it would likely add both structural and plasma stability to the blanket.

The spatial extent of the non-thermal plasma discharge generated at intersections 15b of bare electrodes 18b and dielectric material 14a covered electrodes 12a will determine the spacing between adjacent parallel electrodes of like kind. Preferably, these electrodes will be spaced apart such that there is a small amount of overlap in the corona discharges produced at each intersection, and the spacing will also be a function of the voltage differential applied between electrodes 12a and bare electrodes 18a. Too much overlap in the corona discharge would result in a plasma blanket that incorporates more bare electrodes 18b and dielectric material 14a covered electrodes 12a than is necessary, thus driving up the cost of the plasma blanket. A plasma blanket which has too little or no overlap of corona discharges will have too few electrodes and will not effectively treat the entire surface or object that is contaminated with the biological or chemical agents. The applied power will depend upon the total area of the plasma blanket. It is expected that only about 1 watt/cm$^2$ should be sufficient to treat a surface with the plasma blanket.

While no separation is required between intersections 15b of the bare and dielectric covered electrodes, it is envisioned that nonconductive connectors (not shown) can be used to maintain a desired uniform spacing between bare electrodes 18b and dielectric material covered electrodes 12a. Such connectors can include plastic clips or ties as those of ordinary skill in the art will readily understand.

Figure 4:
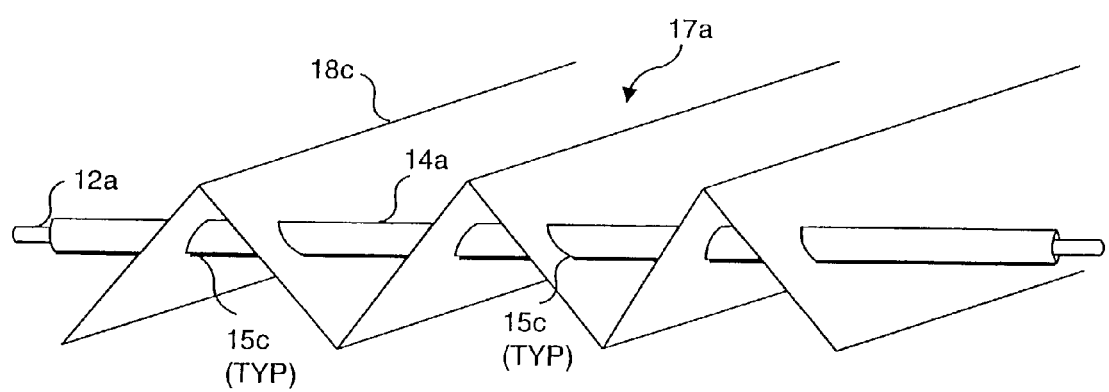
FIG. 4 is an isometric view of a portion of another embodiment of a plasma blanket comprising a distributed plasma reactor of the silent discharge type having a bare electrode in an accordion fold configuration, with a dielectric covered electrode passing through each pleat of the bare electrode.

FIG. 4 illustrates yet another embodiment of a plasma blanket 17a that comprises a single bare electrode 18c that is formed in an accordion fold or pleated configuration, and at least one dielectric material covered electrode 12a. Bare electrode 8c is formed of a metallic foil, a thin metal sheet, a mesh, or other conductive sheet through which electrode 12a covered with dielectric material 14a passes. As with other embodiments, the corona discharge is generated at each of intersections 15c between dielectric material covered electrode 12a and bare electrode 18c. While FIG. 4 illustrates only a single dielectric material 14a covered electrode 12a, it is envisioned that a plurality of such dielectric covered electrodes extending generally parallel to each other will be used. As discussed above, the distance between the pleats of bare electrode 18c and dielectric material 14a covered electrodes 12a preferably creates overlapping corona discharges at each intersection of the bare electrode with the dielectric covered electrodes. Bare electrode 18c can be in point contact with dielectric covered electrode 12a, or there can be a gap between them.

Plasma blanket 17a would have less dimensional flexibility than the woven plasma blanket 17 shown in FIG. 3. However, accordion plasma blanket 17a could be very useful in decontaminating flat surfaces. One advantage of the accordion configuration is that it is a relatively simple design that would be easier to manufacture than woven plasma blanket 17. While not shown, it is envisioned that a non-conducting material may be added to one side of plasma blanket 17a, such that the non-conducting material forms a plane that supports the peaks of the pleats of bare electrode 18c, holding them away from the contaminated surface. This variation would be useful if bare electrode 18c were fabricated from a wire mesh. In this case, reactive species generated by the plasma discharge that are migrating away from the contaminated surface would be reflected from the non-conducting material back toward the contaminated surface, and would pass through bare electrode 18c to reach the contaminated surface. If bare electrode 18c is solid or a non-conducting material is not provided, the reactive species generated by the plasma discharge that are directed away from the contaminated surface would likely not reach the contaminated surface.

FIG. 5 illustrates a preferred embodiment of a plasma blanket 17b. A plurality of distributed plasma reactors 16a are arranged generally parallel to each other and are attached to a flexible substrate 34, such that the distributed plasma reactors cover most of the surface of flexible substrate. Each distributed plasma reactor 16a is identical to the embodiment illustrated in greater detail in FIG. 2. The distributed plasma reactors 16a are spaced apart on flexible substrate 34 such that there is an overlap in the area in which the corona discharges are produced by adjacent distributed plasma reactors. A typical spacing, for example, might be about 0.25 inches; however, the same considerations apply in determining the spacing of the corona discharge generators, as discussed above in regard to the other embodiments. Plasma blanket 17b is energized by a high voltage source 26a, which supplies a voltage of several thousand volts, e.g., 4,000 volts peak-to-peak, applied between the bare electrodes and the dielectric material covered electrodes. Flexible substrate 34 must be non-conductive. The flexible substrate may be a woven material, such as a fiberglass mat, or a non-woven sheet of a material such as a plastic.

The above embodiments have all been distributed plasma reactors using silent corona discharge to generate non-thermal plasma discharges at the intersections of dielectric covered electrodes and bare electrodes. FIGS. 6A, 6B, and 7 illustrate embodiments in which a non-thermal plasma discharge is produced through a slightly different process. FIG. 6A shows a pulse type corona discharge generator 16c that includes an electrode 12b covered with a dielectric material 14a. Electrode 12b preferably comprises a multistrand wire. An end of electrode 12b is unraveled into its individual strands 32. When electrode 12b is energized with a Tesla coil generator 38, a corona discharge 30d emanates from the ends of each individual strand, as shown by a reference numeral 15e. The electric fields are concentrated at the ends of the strands, from which the plasma emanates.

It should also be noted that the pulsed discharge used to energize the preceding embodiment, as discussed above, is distinguishable from prior art uses of a plasma spray to deposit a solid material onto a substrate. The non-thermal plasma generated by pulse type corona discharge generator 16c is not employed for ionizing a solid material that is then deposited on a substrate, but instead is used to ionize ambient air, which produces reactive species that decontaminate a target by destroying biological and/or chemical agents.

FIG. 6B illustrates how corona plasma discharge generator 16c is used to decontaminate a surface 36, which is coupled to a ground 42. By grounding the object to be treated, the zone of the corona discharge is enlarged and corona discharge generator 16c can be disposed at greater distances from surface 36, while remaining effective in destroying chemical and biological contaminants on the surface. It is contemplated that corona discharge generator 16c may be handheld and its corona discharge manually applied and moved over the surface(s) of an object to completely decontaminate those surfaces. Generally, if the object is sitting on the ground, it will be sufficiently grounded to provide the expanded zone of corona discharge shown in FIG. 6B, so that a separate connection to ground through a wire or other conductor will not be required.

While FIGS. 6A and 6B show a dielectric 14a, it is important to understand that in these embodiments, the non-thermal plasma is generated by a pulse discharge device, not a barrier discharge device. Thus, dielectric 14a can be removed without effecting the ability of these embodiments to generate a non-thermal plasma.

FIG. 7 illustrates a plasma blanket comprising distributed plasma reactors of the pulsed discharge type. A plasma blanket 17f includes a flexible substrate 34, which supports a plurality of dielectric spacers 14b and pin or point electrodes 12c. Plasma blanket 17f is energized by Tesla coil generator 38, which is connected to a voltage/power source 26a (which may be a line voltage source, a portable generator, or battery/inverter supply, none of which is shown in the Figure). Preferably, surface 36 is connected to a ground 42 to ensure that zone 15f of the plasma discharge is expanded, in a manner similar to that shown in FIG. 6B. The corona discharge around point electrodes 12e decontaminates surface 36. Dielectric spacers 14b maintain the point electrodes at a fixed spacing apart from surface 36, preventing the point electrodes from shorting to ground by contact with surface 36. It will be apparent that plasma blanket 17f can be moved laterally over surface 36 to cover an expanded area of the surface. In addition, it is contemplated that substrate 34 may be made of a flexible material that will enable the plasma blanket to conform to non-planar surfaces, so long as dielectric spacers 14b maintain the desired spacing between the point electrodes and the grounded surface being decontaminated.

The preceding embodiments have been directed to distributed plasma reactors that have been configured as a plasma blanket to decontaminate surfaces or objects. However, it should be noted that any of the preceding embodiments can also be used to decontaminate a fluid which passes through the non-thermal plasma generated by these distributed plasma reactors. FIGS. 9–12 illustrate embodiments of distributed plasma reactors that are particularly well suited to decontaminate fluid streams. FIGS. 8A and 8B illustrate preferred embodiments of the type of silent corona discharge generators used in the distributed plasma reactors of FIGS. 9–12, in which the bare electrode is a sheet or conducting mesh.

In FIG. 8A, dielectric material 14a covered electrode 12a is disposed generally perpendicular to a bare electrode 18d, which is formed as a sheet. The corona discharge phenomenon arises at an intersection 15d of dielectric material 14a coated electrode 12a and bare electrode 18d. The intersection may comprise a gap, or bare electrode 18*d* can actually be in point contact with dielectric material 14*a*. Bare electrode 18*d* may be formed of a metal foil, a metal mesh, or other conductive sheet-like material. A distributed plasma reactor can be fabricated such that bare electrode 18*d* is the size of the finished reactor. Alternately, a plurality of smaller bare electrodes 18*d* can be mounted in spaced-apart array on a substrate (not shown).

It should be noted that several possibilities arise depending on the characteristics of intersections 15*d* between bare electrode 18*d* and dielectric material covered electrode 12*a*. If intersections 15*d* are rigid and do not allow for movement about the intersection, the resulting distributed plasma reactor will not exhibit much dimensional flexibility. For most fluid stream applications, this issue will not present a problem. It is possible that in some situations, it would be desirable to provide a decontamination system adapted to simultaneously or individually treat a surface and/or a fluid. In such an application, dimensional flexibility would be desirable, and it is preferable that intersections 15*d* between the electrodes be sufficiently flexible to allow dielectric material 14*a* and electrode 12*a* to be moved from a position essentially perpendicular to bare electrode 18*d* as shown in FIG. 8A, to a more acute angle, generally as illustrated in FIG. 8B.

FIG. 9 illustrates a distributed plasma reactor 17*c* comprising a single sheet electrode 18*d* and a plurality of electrodes 12*a* covered with dielectric material 14*a*. Preferably the spacing between the plurality of dielectric material covered electrodes is such that the plasma discharges that are created at the intersections between these electrodes and sheet electrode 18*d* will overlap. Any fluid flowing past these intersections will be exposed to the plasma discharged and biological and/or chemical contaminants conveyed by the fluid will be destroyed thereby.

While distributed plasma reactor 17*c* is expected to be most beneficially employed to treat fluids, bare electrode 18*d* is in a sheet configuration and thus distributed plasma reactor 17*c* could be used to treat surfaces in the same manner as the previously discussed plasma blanket embodiments. If distributed plasma reactor 17*c* is employed to treat a surface, the length of electrodes 12*a* can be adjusted to control the distance between the contaminated surface and the intersections where the corona discharges are produced. The corona discharge phenomenon arises at intersections 15*d* and will have a finite extent. The effective range of the plasma discharge, which is primarily due to the reactive species generated by the ionization of the ambient gas molecules in the plasma region, will determine how much separation between the contaminated surface and intersections 15*d* is permissible. These reactive species will migrate very quickly out of the plasma zone and onto the contaminated surface. The reactive species migrating away from the contaminated surface can be redirected toward that surface. By controlling the length of electrode 12*a*, and thus the separation between the contaminated surface and bare electrode 18*d*, the generated plasma may be selectively directed onto or kept from direct contact with the contaminated surface.

It is contemplated that electrode 12*a* may have a different length above one surface of bare electrode 18*d* than below the opposite surface of bare electrode 18*d*. Distributed plasma reactors 16*b* can then be oriented so that the longer length of electrodes 12*a* are directed toward the contaminated surface to prevent the plasma from direct contacting the contaminated surface, or can be oriented with the shorter length of electrodes 12*a* toward the contaminated surface to direct the plasma onto the contaminated surface, merely by turning the plasma blanket over. Alternately, dielectric material 14*a* covered electrode 12*a* can be slidably attached to bare electrode 18*d*, such that the length of dielectric material 14*a* covered electrode 12*a* between the contaminated surface and bare electrode 18 can be selectively varied by the user.

FIG. 10 illustrates a distributed plasma reactor 17*d* that includes both a plurality of electrodes 12*a* covered with dielectric material 14*a* as well as a plurality of bare sheet electrodes 18*d*. This embodiment allows a distributed plasma reactor to be fabricated that has plasma generating zones not just at the surfaces of the reactor where each dielectric material covered electrode intersects bare sheet electrode 18*d*, but also within interior regions between the plurality of sheet electrodes, where the decontaminating effects of the plasma are provided as well. Such a distributed plasma reactor can be used to treat contaminated fluids flowing through the interior regions, as is shown by a fluid flow 50. It should be noted that fluid flowing through the passages in electrode 18*d* (when the electrode is constructed of a mesh), as shown by a fluid flow 50*a*, will be similarly exposed to the non-thermal plasma and thus, be similarly decontaminated.

Distributed plasma reactor 17*d* would be particularly applicable for use in decontaminating air flowing through a HVAC system, to destroy biological agents (such as disease causing microorganisms, spores, fungi, or allergens) and chemical agents that are conveyed by the air. As above, preferably the spacing between the plurality of dielectric material 14*a* covered electrodes 12*a* is such that overlapping plasma discharges will be created at intersections 15*d* between sheet electrodes 18*d* and dielectric material covered electrodes 12*a*. Furthermore, the spacing between the bare sheet electrodes also should be such that overlapping plasma discharges will be created within the interior region as well.

FIGS. 11 and 12 illustrate a distributed plasma reactor 17*e* that includes an internal treatment volume 48 defined between two spaced-apart bare sheet electrodes 18*e* and 18*f*, which are generally parallel to each other. Distributed plasma reactor 17*e* also has a plurality of electrodes 12*a* covered with dielectric material 14*a* that pass through upper bare sheet electrode 18*e* and lower bare sheet electrode 18*f*. Preferably, distributed plasma reactor 17*e* includes sufficient dielectric material covered electrodes 12*a* that are spaced so as to provide an overlap of the resulting corona discharge plasma zones, which will be particularly effective in decontaminating a fluid flowing through internal treatment volume 48 that is contaminated with biological agents (such as disease causing microorganisms, spores, fungi, or allergens) and/or chemical agents. Sheet electrodes 18*e* and 18*f* should be sufficiently close together such that the entire internal treatment volume 48 is saturated with non-thermal plasma. Distributed plasma reactor 17*e* is thus particularly applicable to decontaminating air or gas streams in an HVAC system or if made smaller, for use in an air purifying respirator or gas mask, to decontaminate air breathed by personnel that may convey biological or chemical warfare agents. This embodiment is also useful for decontaminating a liquid having minimal conductivity. It should be noted that while the dielectric 14*a* covered electrodes 12*a* comprise a barrier discharge corona generator (as shown schematically in FIG. 1), the embodiment detailed in FIGS. 11 and 12 would operate if a pulsed corona discharge generator (as shown in FIG. 6A) was used instead.

FIG. 12 illustrates how the plasma discharges of distributed plasma reactor 17*e* can be used to decontaminate a fluid. When distributed plasma reactor 17e is energized by applying several thousand volts (A/C) of potential between electrodes 12a and bare sheet electrodes 18e/18f, a plasma discharge is produced in a zone 30a above bare sheet electrode 18e, at a zone 30b within internal treatment volume 48, and in a zone 30c underneath bare sheet electrode 18f at each intersection 15d. Plasma discharge in zone 30b is perhaps most useful in decontaminating fluid flowing through internal treatment volume 48, as shown by fluid flow 50. The fluid can also be caused to flow through openings in the upper surface of bare sheet electrode 18e and bare sheet electrode 18f (when such electrodes are in a mesh configuration), through zones 30a and 30c, as is shown by fluid flows 50a. While not shown in FIG. 11 or 12, it should be noted that multiple internal treatment volumes 48 can be created with the addition of further sheet electrodes disposed adjacent and generally parallel to either sheet electrode 18e or 18f.

Internal treatment volume 48 may be filled with a packing material to improve the reactor performance. The resulting improvement in performance is due to increasing the residence time of the contaminants within the plasma zone of internal treatment volume 48. Additionally, a catalytic packing material can be selected to further enhance the reactor performance.

The concept and benefits of altering residence time are well established in the art of fluid and gas chromatography. It is known that when a contaminant in a carrier fluid is introduced into a packed column of granular material, the contaminant interacts with the packing to slow its procession through the packed column relative to the carrier fluid. The primary reason for the difference in residence times is that a carrier fluid is selected so that the size of the contaminant molecules are substantially larger than the size of the carrier fluid molecules. If the contaminant is known, then the packing material may be selected such that the packing material has greater affinity for the contaminant than the carrier fluid, so that the passage of the contaminant through the packed column is further impeded. When internal volume 48 of plasma reactor 17e is filled with a packing material, this chromatographic affect permits higher fluid flow rates to be attained, while maintaining a very high processing efficiency for the contaminant, which resides in the plasma for a longer period time.

The form of the packing material can be granular, tubular, ring, spheroidal or spherical, fibrous, foam or aggregate. Preferably the packing material has a resistivity greater than a like volume of the fluid being processed and a dielectric constant equal to or greater than that of the fluid (for air, the dielectric constant equals one). The packing surface may be inert or catalytic in nature. Surfaces impregnated with active metal catalysts have been demonstrated to be more effective than inert or unimpregnated packing materials. Pyrex beads, pyrex rings, platinum-palladium-rhodium catalyst spheroids, alumina spheroids, and other materials have been successfully utilized as packing materials in thermal and plasma reactor columns and should be equally effective in the present invention. The packing material can be porous or nonporous; however, greater adsorptive capability is preferred for packings used in high performance plasma discharge reactors. A packing material can improve reactor performance due to catalytic effects alone, rather than due to any adsorptive capability. Preferably, a packing material the exhibits both adsorptive and catalytic properties will be selected.

A particular advantage exhibited by the combination of a packed treatment area and a distributed plasma reactor is the surface cleaning of the packing by the non-thermal plasma. A common problem in thermal catalytic reactors is that the packing eventually becomes blocked or poisoned by contaminant condensates or reaction products, such as inorganic salts or oxides. The reactive species generated by the non-thermal plasma that destroy the contaminants also interact with the surfaces of the packing material to purge any such condensates or reaction products. The continual cleaning of the surfaces by these reactive species prevents saturation or poisoning of the packing material. This cleaning process insures optimum performance of distributed plasma reactor 17e.

FIG. 13 illustrates an embodiment of a distributed plasma reactor 17g of the pulsed discharge type in which an internal treatment volume is filled with a packing material that comprises a plurality of small "secondary" coil covered dielectrics. A "primary" helical coil 64 surrounds an internal treatment volume 58. Primary coil 64 is connected to and energized by tesla coil 38 at a first end, and connected to ground 42 at a second end. Prior to filling internal treatment volume with the packing material, a contaminated object 62 is placed inside internal treatment volume 58. Preferably, contaminated object 62 is raised above the floor of internal treatment volume 58 by supports 60, to ensure that the lower surfaces of contaminated object 62 are bathed in plasma. Once contaminated object 62 is in position, all of the remaining void or space within internal treatment volume 58 is filled with a plurality of small secondary coils 66. When primary helical coil 64 is energized by tesla coil 38, inductive coupling between the primary helical coil and the plurality of small secondary coils 66 causes internal treatment volume 66 to be bathed in a non-thermal plasma. This plasma effectively treats contaminated object 62 in the manner described above.

The terms primary coil and secondary coil have been used to describe the coils in this particular embodiment because of the similarity that this apparatus shares with a tesla coil, namely the inductive coupling between a primary coil and a secondary coil via an air gap. One benefit of this embodiment is that the inductive coupling helps create a large, stable plasma region. This particular embodiment does require high excitation voltages and high power levels, and as such, is expected to be better suited to non-portable applications. However, this embodiment does share the feature with other embodiments that the non-thermal plasma is generated at a plurality of locations distributed throughout a treatment volume.

Once the treatment of an object is completed, the secondary coils are removed from the treatment volume so that the decontaminated object may be removed. The secondary coils are saved for re-use. It is also contemplated that instead of placing an object inside of the internal treatment volume, a fluid could be passed through the internal treatment volume and similarly decontaminated.

FIG. 14 is an isometric schematic view of a one of the plurality of small secondary coils used to fill the remaining void or space of internal treatment volume 58 in distributed plasma reactor 17g. Secondary coil 66a includes many coils 15g of a conductor extending around a dielectric core 70, which is preferably in the form of either an ellipse, a rod, or a bead. Coils 15g can be of a fine wire or a metallic trace deposited on the surface of dielectric core 70 and may optionally be covered with a dielectric layer (not shown).

FIG. 15 is a isometric schematic view of one embodiment of a primary coil 64a to be used in conjunction with distributed plasma reactor 17*g*. This embodiment comprises a coil with a plurality of spark gaps 68. The high voltage this embodiment requires can be generated by adding more turns to primary coil 64. One drawback related to this embodiment is an inherent reduction in the rate at which the primary coil can be switched. As an alternative, primary coil 64*a* can be used. Primary coil 64*a* includes a plurality of spark gaps around the perimeter of distributed plasma reactor 17*g*.

FIG. 16 is a block diagram illustrating the functional components of a distributed plasma reactor decontamination system in accord with the present invention. A battery 20 (or other power source) is connected to a control logic and electric interface 22. A user interface 24 is connected to the control logic and electric interface, enabling a user to adjust the voltage level of the system, set the pulse duration, and control other parameters such the duration of the decontamination process. Logic control interface 22 is connected to a high voltage inverter 26, which converts the battery voltage, e.g., 12 volts direct current, to a high voltage signal, e.g., 4,000 volts peak-to-peak. The output voltage from high voltage inverter 26 is attached to a distributed plasma reactor 28, so that the potential difference is applied between the bare electrodes and the dielectric material covered electrodes. While a battery allows the distributed plasma reactor to be more readily portable, the distributed plasma reactor can be adapted to be energized by other power sources, such as a line voltage source available at the location of the contamination, or a portable generator.

In an experiment conducted with a distributed plasma reactor like the embodiment shown in FIG. 5, a plasma blanket measuring about 3 in. per side was fabricated. A 5 watt power source was used to energize the corona discharge plasma generators in the plasma blanket with a voltage of about 4,000 volts peak-to-peak. It was found that a slide contaminated with *Bacillus globigii* was substantially decontaminated by exposure to the plasma discharge of the plasma blanket for a time interval of only about 5 minutes.

It will be apparent that a personal decontamination system can be provided with the present invention by making each of the elements shown in FIG. 13 sufficiently small and compact to be carried by an individual. This decontamination system can then be incorporated into a gas mask to decontaminate ambient air conveying biological or chemical agents. Larger portable decontamination systems can use a plasma blanket embodiment of a distributed plasma generator to decontaminate surfaces or objects that have been contaminated with biological or chemical agents. By using a flexible plasma blanket that is draped over or wrapped about an object, irregularly-shaped objects, including military vehicles such as tanks, can be decontaminated. Distributed plasma generators can also be incorporated into HVAC systems through which air is supplied to vehicles or buildings to decontaminate the air by destroying biological or chemical agents carried by the air. Particles such as seeds or herbs can be decontaminated by exposure to the plasma discharge produced by the present invention to destroy harmful agents such as insecticides, herbicides, molds and fungi that are on the surface of the seeds or herbs. The present invention can also be used for decontaminating soil particles that have become contaminated by exposure to chemicals (or other contaminants) released into the soil, or for preparing soils for planting by destroying molds naturally occurring in the soil. Plasma decontamination of fluids, such as air, can be carried out with any of the embodiments of the present invention in which a fluid stream can be conveyed through a region of plasma discharge, particularly the embodiments shown in FIGS. 9–12, to destroy biological or chemical contaminants in the fluid.

One of the byproducts of a plasma discharge is ozone. Accordingly, the present invention is also useful for generating ozone, which is usable to oxidize contaminants in drinkable liquids or on foodstuffs.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention claimed is:

1. A method for decontaminating a surface on which either a biological or chemical toxic agent has been deposited, comprising the steps of:

(a) providing a power source that produces a voltage sufficiently great to generate a non-thermal plasma discharge and a plasma blanket that is sufficiently flexible to be able to be draped and wrapped around an object, the plasma blanket comprising a generally, sheet non-thermal plasma generator configured to distribute a non-thermal plasma discharge to the surface adjacent to the plasma blanket when activated by the power source;

(b) positioning the plasma blanket adjacent to the surface that is to be decontaminated; and (c) activating the non-thermal plasma generator with the power source, producing the non-thermal plasma discharge that destroys the toxic agent, thereby decontaminating the surface.

2. The method of claim 1, wherein the surface is non-planar and is part of an irregularly-shaped object, further comprising the step of draping the plasma blanket over the irregularly-shaped object, so the plasma blanket is proximate to the non-planar surface.

3. The method of claim 1, wherein the non-thermal plasma generator is activated for a time interval of less than ten minutes to decontaminate the surface.

4. The method of claim 1, wherein the non-thermal plasma generator is a distributed plasma reactor, comprising a plurality of electrodes configured to generate a non-thermal plasma at a plurality of different locations distributed across the plasma blanket, each of the plurality of electrodes being adapted to be disposed adjacent to the surface that is to be decontaminated, such that non-thermal plasma generated by the plurality of electrodes is distributed across a plurality of locations on the surface to be decontaminated.

5. The method of claim 1, wherein the non-thermal plasma discharge is generated using a high voltage pulse.

6. The method of claim 1, further comprising the step of moving the non-thermal plasma generator over the surface, to decontaminate a larger area of the surface.

* * * * *